Figure 1:
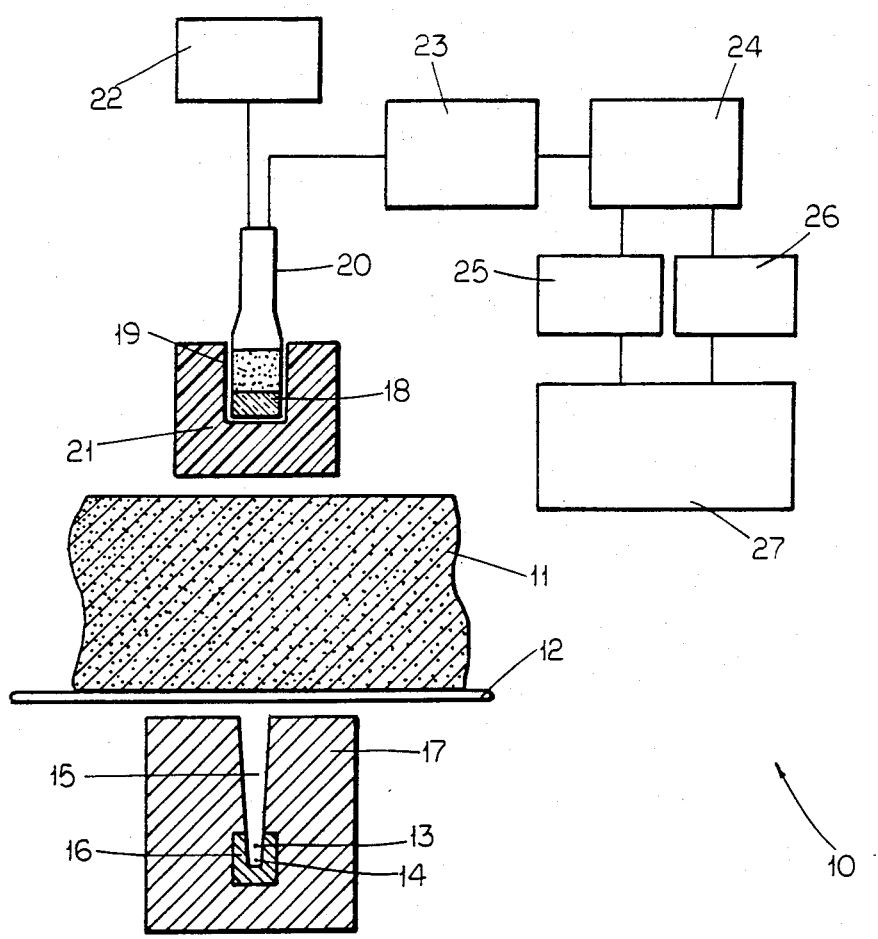

United States Patent [19]

Sowerby

[11] Patent Number: 4,884,288
[45] Date of Patent: Nov. 28, 1989

[54] NEUTRON AND GAMMA-RAY MOISTURE ASSAY

[75] Inventor: Brian D. Sowerby, Kareela, Australia

[73] Assignee: Commonwealth Scientific and Industrial Research Organization, Campbell, Australia

[21] Appl. No.: 946,966

[22] Filed: Dec. 29, 1986

[30] Foreign Application Priority Data

Dec. 31, 1985 [AU] Australia .............................. PH4049

[51] Int. Cl.$^4$ ...................... G01N 23/06; G01N 23/09
[52] U.S. Cl. ......................................... 378/51; 378/53; 250/390.05
[58] Field of Search ............................ 378/51, 52, 53; 250/390 D, 390 I, 390 J

[56] References Cited

FOREIGN PATENT DOCUMENTS

| 0063440 | 4/1982 | Japan | 250/390 D |
| 0154347 | 12/1984 | Japan | 250/390 D |
| 0230146 | 12/1984 | Japan | 250/390 D |
| 0186737 | 9/1985 | Japan | 250/390 D |

OTHER PUBLICATIONS

Knoll, Glen F., *Radiation Detection and Measurement*, John Wiley & Sons, New York, 1979, pp. 554–556.
English Translation of Japanese Patent 60-186737.

Primary Examiner—Carolyn E. Fields
Assistant Examiner—Joseph A. Hynds
Attorney, Agent, or Firm—Ladas & Parry

[57] ABSTRACT

A method and apparatus is disclosed for determining the moisture content of a substance irradiated by a fast neutron and gamma ray source wherein a fast neutron moderator is positioned in the path of the fast neutrons and gamm rays transmitted through the substance. A unitary thick Li glass or LiI glass detector is positioned behind or surrounded by the fast neutron moderator and detects both slow neutrons and gamma rays. Simplified counting circuitry utilizing a single channel analyser determines the intensities of the detected slow neutrons and gamma rays enabling the moisture content of the substance.

16 Claims, 2 Drawing Sheets

NEUTRON AND GAMMA-RAY MOISTURE ASSAY

This invention relates to a system and a method for determining the moisture content of a substance.

Measurements of, and in particular on-line measurements of, the moisture contents of various types of substances are required for a range of industrial methods. One particular technique for measuring moisture utilises a thermal neutron gauge which detects thermal neutrons resulting from the moderation of fast neutrons by collision with hydrogen atoms.

This technique depends on the much greater slowing-down power of hydrogen compared with other atoms. Some disadvantages of this technique are restricted sample penetration, density correction difficulties, sensitivity to temperature changes and inaccuracies caused by variations in the concentration of elements of high thermal neutron absorption cross section.

A moisture gauge based on the simultaneous transmission of fast neutrons and gamma-rays overcomes many of the limitations of thermal neutron moisture gauges. A report in the literature on a gauge of this type is by Tominaga, H. et al., International Journal of Applied Radiation Isotopes, Vol. 34 (1983) 429. This gauge consisted of a single Cf-252 source and a single organic liquid scintillator (NE 213). Pulse shape discrimination (PSD) electronics were employed to selectively detect fast neutrons and gamma-rays. This system has the advantages of (i) a relatively high fast neutron detection efficiency and (ii) the neutron and gamma-ray beams completely overlap. However PSD circuitry is very complex and it requires a high degree of skill to set up and optimise such circuitry and to keep it stable. This gauge in combination with PSD circuitry was used to measure moisture content in coke in an iron making process. The results showed that the precision of moisture determination was improved several times compared to ordinary thermal neutron moisture gauges.

A method of measuring fast neutron transmission and a separate measurement of gamma-ray transmission has also been reported by Corey, J. C. and Hayes, D. W., Deep-Sea research, Vol. 17 (1970) 917 and Corey, J. C., Boulogne, A. R. and Horton, J. H., Water Resources Research, Vol. 6 (1970) 223. These workers used a plastic/ZnS fast neutron detector (NE451) and a NaI(Tl) gamma-ray detector. The disadvantages of this method are the very low fast neutron detector efficiency and non-overlapping volume of the neutron and gamma-ray beams.

Fast neutron transmission alone was reported by Williams, R. B., Journal of Radioanalytical Chemistry, Vol. 48 (1979) 49, using a He-3 detector surrounded by paraffin wax. No gamma-ray scattering was measured and measurements were made on iron ore sinter samples of constant thickness.

It is an object of this invention to provide a system for measuring the moisture content of a substance which ameliorates the disadvantages of the above prior art.

In a first embodiment according to this invention there is provided a system for measuring the moisture content of a substance comprising a fast neutron and gamma-ray source or sources, a slow neutron detector which can also detect gamma rays surrounded by a fast neutron moderator positioned in the path of fast neutrons and gamma-rays emitted by the source or sources after interaction of the emitted fast neutrons and gamma-rays with the substance, counting means associated with the detector for determining the intensities of the detected fast neutrons and gamma-rays and calculating means associated with the counting means for calculating the moisture content of the substance from the intensities. In a second embodiment according to this invention there is provided a method for measuring the moisture content of a substance comprising:

(a) irradiating one side of the substance with fast neutrons and gamma-rays;

(b) detecting said fast neutrons and gamma-rays after transmission through the substance characterised in that slow neutrons corresponding or proportional to the transmitted fast neutrons and gamma-rays are detected by a slow neutron detector which can also detect gamma rays surrounded by a fast neutron moderator;

(c) simultaneously determining the intensities of the detected slow neutrons and gamma-rays; and (d) calculating the moisture content of the substance from the intensities of (c).

The invention finds particular application in the measurement of the moisture content of coke.

In this specification a reference to coke is also a reference to coal.

The term gamma-rays in this specification encompasses gamma-rays and X-rays. The word interaction in this specification and claims includes transmission, absorption, reflection, scattering and diffraction.

Preferably the detector surrounded by the fast neutron moderator is positioned on the opposite side of the substance and as a result detects fast neutrons and gamma-rays transmitted by the substance. The detector can be a Li glass or LiI detector surrounded by a fast neutron moderator since it has the advantage that it can simultaneously detect slow neutrons and gamma-rays.

A hydrogenous fast neutron moderator such as paraffin or polyethylene is preferred. The fast neutron moderator slows down fast neutrons and the resulting slow neutrons are detected by a Li glass or LiI detector via the $^6$Li(n,$\alpha$)$^3$H reaction. The thickness of moderator can be selected to provide near optimum efficiency for fast neutrons as reported by Bramblett, R. L., Ewing, R. I. and Bonner, T. W., Nucl. Instr. Methods, Vol. 9 (1960) 1. A paraffin thickness of 80 to 100 mm is suitable for $^{252}$Cf neutrons.

Gamma-rays interact with a Li glass or LiI detector mainly via Compton scattering and a detector thickness of greater than 5 mm is preferred to achieve reasonable gamma-ray detection efficiency. The detector thickness is increased to increase sensitivity. The gamma-ray transmission measurement is used to determine the mass per unit area of sample in the radiation beam. Measurements may be made with or without a separate gamma-ray source (such as Cs-137). Measurements without a separate gamma-ray source utilise the gamma-radiation from the neutron source for the measurement of mass per unit area.

The type of neutron source can be selected to suit the particular application. Some possible sources are Cf-252 (average neutron energy ~0.5 MeV) Am-241/Be(4.5 MeV) and a neutron generator (14 MeV). The source is selected to give the appropriate transmission factor and intensity, the higher energy sources being suited to larger thicknesses of material to be measured.

Preferably the intensities of transmitted fast neutrons and gamma-rays are determined in selected non overlapping energy ranges in the detector output. It is especially preferred that the selected energy range for determining the intensities of fast neutrons includes a fast neutron intensity peak.

The system of Tominaga, H. et al, International Journal of Applied Radiation Isotopes, Vol. 34 (1983) 429 necessarily utilises highly complex PSD electronics whereas an advantage of the system of this invention is that it can use a standard gain stabiliser and dual channel counters for the counting means.

Conveniently the system of this invention can be used to determine on-line the moisture content of coke in the hostile environment of a steel plant. In comparison maintaining stable PSD electronics is difficult even in a laboratory environment.

The intensity $I_n$ of a collimated beam of fast neutrons transmitted through sample coal of density $\rho$ and thickness x has been calculated by dividing the incident neutron energy spectrum into 20 intervals. As the total cross sections for the various elements are similar at MeV neutron energies, the neutron mass absorption coefficients are approximately inversely proportional to atomic weight and therefore fast neutron attenuation is dominated by the light elements, particularly hydrogen. It can be shown that a calibration equation for a fast neutron and gamma-ray transmission gauge can be of the form:

$$\text{Moisture} = a\frac{\ln(I_n/I_{on})}{\ln(I_\gamma/I_{o\gamma})} + b\ln(I_n/I_{on}) + c(I_n/I_{on}) + d \quad (1)$$

where a, b, c and d are constants; $I_n$ and $I_{on}$ are measured neutron intensities with and without a sample present respectively; $I_\gamma$ and $I_{o\gamma}$ are measured $\gamma$-ray intensities with and without a sample present respectively. Calculations for a $^{252}$Cf source and coke sample of thickness 30–50 cm and moisture 1–17 wt% showed that the method should be able to determine moisture to within 0.26 wt% using equation (1).

Note that changes in the form of calibration equation (1) often do not significantly alter the analysis error. For example, exclusion of the third term in eqn. (1) increases the error by only about 5% relative.

The system of the invention is particularly suited for the following applications:

(a) On-line determination of moisture in coke. The technique is well suited to the determination of coke moisture in hoppers with coke thickness from 0.1 to about 1.5 m.

(b) On-line determination of moisture in other materials such as iron ore, sinter mix and coal. Measurement can be made on conveyor belts, in hoppers or on a moving sinter bed. Materials containing variable bound hydrogen (such as coal) may require additional measurements (e.g. ash) to determine the bound hydrogen concentration.

(c) Determination of the lowest atomic number element in a high atomic number matrix. For example, carbon in steel may be determined provided no elements of lower atomic number are present.

Figure 2:
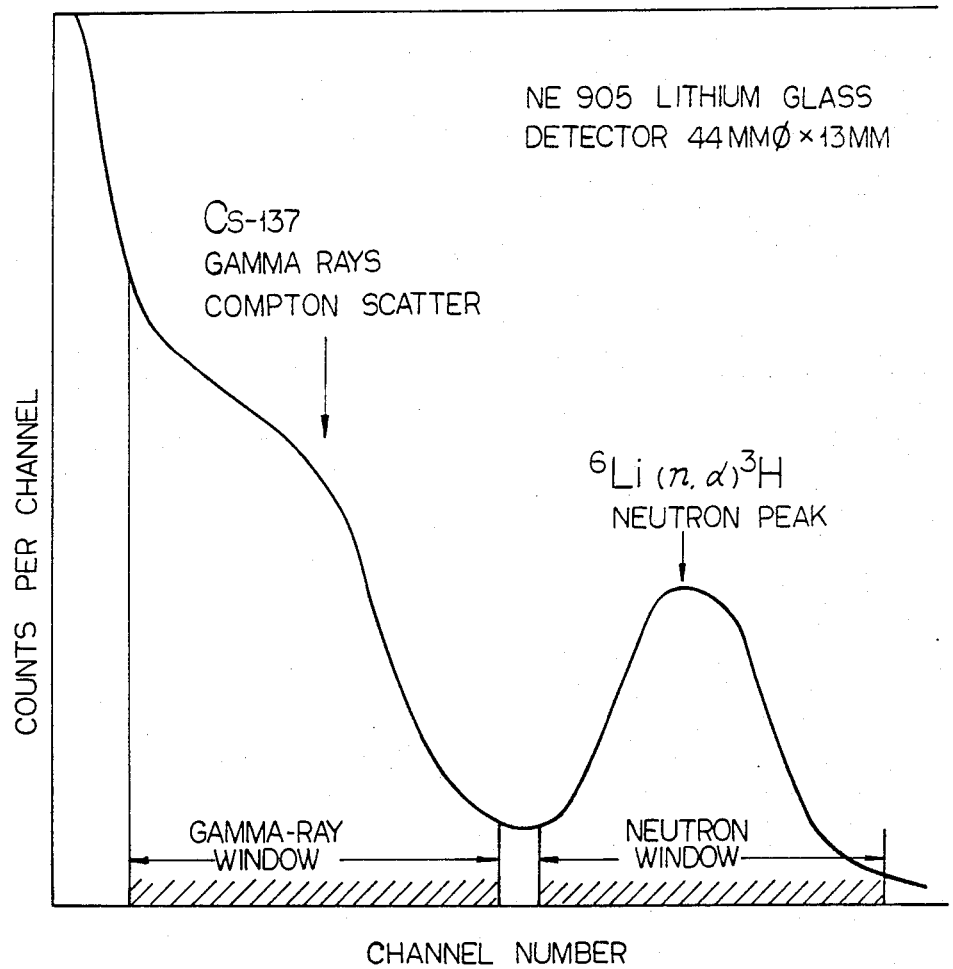

A preferred embodiment of this invention and a comparative example will now be described with reference to the following drawings in which:

FIG. 1 is a schematic drawing of a system to determine the moisture content of coke; and FIG. 2 is a typical pulse height spectrum obtained using a Li glass detector showing two suitable windows for the determination of fast neutron and gamma-ray intensities.

Referring to FIG. 1 a system 10 for measuring the moisture content of coke 11 on conveyor 12 includes a $^{252}$Cf fast neutron source 13 and a $^{137}$Cs gamma-ray source 14 in a shield having an upwardly directed opening 15 positioned under conveyor 12. The shield consists of an inner lead shield portion 16 and an outer borated paraffin shield portion 17.

A Li glass detector consisting of a Li glass scintillator (NE905) 18, perspex light guide 19 and photomultiplier tube 20 is positioned wherein scintillator 18 is above coke 11 and opposite opening 15 so as to be in the path of fast neutrons and gamma-rays transmitted by coke 11. Scintillator 18 is surrounded by paraffin wax or polyethylene moderator 21 which slows down fast neutrons and the resultant slow neutrons interact with scintillator 18 according to the $^6$Li(n, $\alpha$)$^3$H reaction. Light photons resulting from $\alpha$-particles from this reaction are directed to and detected by tube 20 via guide 19.

A thickness of 80 mm–100 mm is chosen for moderator 21 to provide near optimum efficiency for slowing fast neutrons. Tube 20 is powered by high voltage source 22. The output from tube 20 is fed to neutron and gamma-ray counters 25 and 26 via gain stabilised amplifier 23 and single channel analysers 24. To determine moisture content, coke 11 is irradiated by fast neutrons and gamma-rays emanating from sources 13 and 14 respectively. Fast neutrons and gamma-rays which are transmitted through coke 11 are simultaneously detected by the Li glass detector. The intensities of the detected fast neutrons and gamma-rays are determined by counters 25 and 26 respectively in selected substantially non-overlapping energy ranges. The energy range for determining the intensities of fast neutrons is selected so as to include a fast neutron intensity peak to achieve increased accuracy. A typical pulse height spectrum obtained by using an NE905 Li glass scintillator in a detector is shown in FIG. 2. The moisture content of coke 11 is calculated by computer 27 from the values of the neutron and gamma-ray intensities obtained from a pulse height spectrum of the type shown in FIG. 1 according to calibration equation (1) or according to the following equation:

$$\text{Moisture Content} = a\ln(I_n/I_{on}) + b\ln(I_\gamma/I_{o\gamma}) + cI_n + dI_\gamma + e \quad (2)$$

where a, b, c, d and e are constants, $I_n$ and $I_{on}$ are the measured neutron intensities with and without coke present respectively, and $I_\gamma$ and $I_{o\gamma}$ are the measured gamma-ray intensities with and without coke present respectively.

COMPARATIVE EXAMPLE

A number of neutron and gamma-ray transmission systems have been used to evaluate the effects of collimation, detector type, sample thickness and moisture range on the accuracy of coal and coke moisture determination. A direct comparison of the NE213/PSD and Li glass detection systems has not been made although both have been compared to a detection system employing separate neutron and gamma-ray detectors.

In geometry A (Table 1) and 51×51 mm NE213 liquid scintillator was used and the neutron and $\gamma$-ray pulses separated using commercial PSD circuitry. However considerable difficulty was experienced in maintaining stability in this equipment. Comparison of the results for geometries A and B (Table 1) show no deterioration in accuracy when the NE213 liquid scintillator is replaced by separate neutron and gamma-ray detectors. The fast neutron detector comprises a He-3 detector surrounded by 100 m thickness paraffin and the gamma-ray detector comprised 76×76 mm NaI(Tl).

In geometries C and D the 500 mm long collimator of geometries A and B was replaced by a shorter collimator and the source strengths halved. These changes did not significantly affect the accuracy of the gauge for coal moisture and resulted in reduced analysis times. Measurements carried out on crushed coke (particle size minus 10 mm) show that coke moisture can be determined to within about 0.3 wt% using either the separate He-3 and NaI(Tl) detectors or by using a single Li glass detector. In both geometries C and D, the time required to achieve a counting statistical error of 0.2 wt% moisture is about 100 sec.

These results show that equivalent accuracies can be achieved using either the NE213/PSD detection system or the simpler Li glass detection system.

TABLE 1

Summary of experimental results comparing various detector systems for the determination of moisture in coal and coke using fast neutron and gamma-ray transmission

| Geometry | Comparison of Ne213/PSD He-3/NaI detectors | | Comparison of and He-3/NaI and Li glass detectors | |
|---|---|---|---|---|
| | A | B | C | D |
| Neutron and gamma-ray detecotr(s) | NE213 | ³He* and NaI(Tl) | ³He* and NaI(Tl) | Li glass* |
| Collimator length (mm) | 500 | 500 | 200 | 200 |
| Collimator diameter (mm) | 14–38 | 14–38 | 20–60 | 20–60 |
| Source detector spacing (m) | 720 | 850 | 890 | 890 |
| Sample | Coal | Coal | Coke | Coke |
| Moisture range (wt %) | 4–25 | 0–17 | 1–16 | 1–16 |
| Thickness range (mm) | 7.5–15 | 5–15 | 30–50 | 20–50 |
| Rms deviation** (wt % H₂O) | 1.01 | 0.91 | 0.26 | 0.31 |

*Surrounded by 100 m thick paraffin
**Obtained using equation (1)

I claim:

1. A system for measuring the moisture content of a substance comprising:
   a fast neutron and gamma-ray source disposed in the vicinity of the substance to irradiate the substance with fast neutrons and gamma-rays, a fast neutron moderator positioned in the path of the fast neutrons and gamma-rays transmitted through the substance,
   a unitary Li glass or LiI slow neutron detector having a thickness ranging from 5 mm to 50 mm which can also detect gamma-rays positioned behind or surrounded by the fast neutron moderator to detect slow neutrons, corresponding to or proportional to fast neutrons transmitted through the substance and to detect gamma-rays transmitted through the substance,
   counting means operatively associated with the detector for determining the intensities of the detected gamma-rays and the detected slow neutrons, and
   calculating means operatively associated with the counting means for calculating the moisture content of the substance from the intensities.

2. The system as defined in claim 1 wherein the detector is Li glass.

3. The system as defined in claim 1 wherein the detector is disposed opposite the source.

4. The system as defined in claim 1 wherein the detector is of a thickness greater than 5 mm.

5. The system as defined in claim 1 wherein the counting means is set up to detect the intensities of the slow neutrons and the transmitted gamma-rays in selected substantially non-overlapping energy ranges.

6. The system as defined in claim 5 wherein the energy range for determining the intensities of slow neutrons is selected so as to include a slow neutron intensity peak.

7. The system as defined in claim 1 wherein the substance is coal or coke and the calculating means calculates the moisture content of the coal or coke according to the algorithm:

$$\text{Moisture} = a \frac{\ln(I_n/I_{on})}{\ln(I_\gamma/I_{o\gamma})} + b\ln(I_n/I_{on}) + c(I_n/I_{on}) + d$$

where a, b, c and d are constants; $I_n$ and $I_{on}$ are measured neutron intensities with and without a sample of said coal or coke present respectively; and $I_\gamma$ and $I_{o\gamma}$ are measured gamma-ray intensities with and without a sample of the coal or coke present respectively.

8. A system as defined in claim 1 wherein said slow neutron detector has a thickness ranging from 5 mm to 40 mm.

9. A method for measuring the moisture content of a substance comprising:
   (a) irradiating a side of the substance with gamma-rays and fast neutrons;
   (b) detecting gamma-rays transmitted through the substance and detecting slow neutrons, corresponding to or proportional to fast neutrons transmitted through the substance, with a unitary Li glass or LiI slow neutron detector having a thickness ranging from 5 mm to 50 mm which can also detect gamma-rays, said detector being surrounded by or positioned behind a fast neutron moderator disposed in the path of the transmitted gamma-rays and the transmitted fast neutrons;
   (c) determining intensities of the detected gamma-rays and the detected slow neutrons; and
   (d) calculating the moisture content of the substance from the determined intensities of (c).

10. The method as defined in claim 9 wherein the detector is LiI.

11. The method as defined in claim 9 wherein a gamma-ray and fast neutron source is disposed in the vicinity of the substance whereby gamma-rays and fast neutrons emanating from the source irradiate a side of the substance adjacent to the source and wherein the detector is disposed on the opposite side of the substance to the source.

12. The method as defined in claim 9 wherein the detector is of a thickness greater than 5 mm.

13. The method as defined in claim 9 wherein counting means for determining the intensities of the detected gamma-rays and slow neutrons is operatively associated with the detector and wherein the counting means is set up to detect the intensities of the detected gamma-rays and slow neutrons in selected non-overlapping energy ranges.

14. The method as defined in claim 13 wherein the selected energy range for determining the detected slow neutrons includes a slow neutron intensity peak.

15. The method as defined in claim 9 wherein the substance is coal or coke and the moisture content of the coal or coke is calculated according to the algorithm:

$$\text{Moisture} = a\frac{\ln(I_n/I_{on})}{\ln(I_\gamma/I_{o\gamma})} + b\ln(I_n/I_{on}) + c(I_n/I_{on}) + d$$

where a, b, c and d are constants; $I_n$ and $I_{on}$ are measured neutron intensities with and without a sample of said coal or coke present respectively; and $I_\gamma$ and $I_{o\gamma}$ are measured gamma-ray intensities with and without a sample of the coal or coke present respectively.

16. The method as defined in claim 10 wherein a gamma-ray and fast neutron source is disposed in the vicinity of the substance whereby the gamma-rays and fast neutrons emanating from the source irradiate a side of the substance adjacent to the source and wherein the detector is disposed on the opposite side of the substance to the source.

* * * * *